United States Patent [19]

Fost et al.

[11] Patent Number: 5,405,983

[45] Date of Patent: Apr. 11, 1995

[54] SILICONE MODIFIED PHOSPHOLIPID COMPOSITIONS

[75] Inventors: Dennis L. Fost, Ridgewood; Abe Berger, Summit, both of N.J.

[73] Assignee: Mona Industries, Inc., Paterson, N.J.

[21] Appl. No.: 174,934

[22] Filed: Dec. 28, 1993

[51] Int. Cl.⁶ .............................................. C07F 7/10
[52] U.S. Cl. ..................................................... 556/405
[58] Field of Search ........................................ 552/405

[56] References Cited

U.S. PATENT DOCUMENTS

| | | |
|---|---|---|
| 2,488,449 | 11/1949 | Trautman . |
| 2,768,193 | 10/1956 | Gilbert . |
| 2,843,615 | 7/1958 | Linville . |
| 3,067,229 | 12/1962 | Fekete . |
| 3,113,139 | 12/1963 | Birum et al. . |
| 3,389,160 | 7/1968 | Reid . |
| 3,441,537 | 4/1969 | Lengnick . |
| 3,492,193 | 1/1970 | Tesoro ............................ 556/405 X |
| 3,716,569 | 2/1973 | Redmore et al. ................... 556/405 |
| 3,839,388 | 10/1974 | Ritzsche et al. . |
| 3,890,269 | 7/1975 | Martin . |
| 4,006,176 | 2/1977 | Heckert et al. . |
| 4,045,460 | 8/1977 | Kleinstück . |
| 4,093,641 | 6/1978 | Plueddemann . |
| 4,104,296 | 8/1978 | Pike . |
| 4,185,087 | 1/1980 | Morlino . |
| 4,234,502 | 11/1980 | Kappler et al. . |
| 4,282,366 | 8/1981 | Eudy . |
| 4,342,742 | 8/1982 | Sebag et al. . |
| 4,384,130 | 5/1983 | Martin . |
| 4,417,066 | 11/1983 | Westall . |
| 4,511,727 | 4/1985 | Martin . |
| 4,654,161 | 3/1987 | Kollmeier et al. . |
| 4,847,397 | 7/1989 | Sawaragi et al. . |
| 4,866,192 | 9/1989 | Plueddemann et al. . |
| 4,889,942 | 12/1989 | Gutek et al. . |
| 4,891,166 | 1/1990 | Schaefer et al. . |
| 4,898,614 | 2/1990 | Halloran et al. . |
| 4,900,857 | 2/1990 | Klett ..................................... 556/405 |
| 4,996,342 | 2/1991 | Ching et al. . |
| 5,008,424 | 4/1991 | Halloran et al. . |
| 5,039,761 | 8/1991 | Ono et al. . |
| 5,068,377 | 11/1991 | Kawamoto et al. . |
| 5,070,171 | 12/1991 | O'Lenick, Jr. . |
| 5,087,715 | 2/1992 | Snow . |
| 5,091,493 | 2/1992 | O'Lenick, Jr. et al. . |
| 5,093,452 | 3/1992 | O'Lenick, Jr. . |
| 5,099,051 | 3/1992 | Beck et al. . |
| 5,101,056 | 3/1992 | Kampling et al. . |
| 5,137,951 | 8/1992 | Pastor et al. ....................... 556/405 X |
| 5,151,210 | 9/1992 | Steuri et al. . |

*Primary Examiner*—Paul F. Shaver
*Attorney, Agent, or Firm*—Franklyn Schoenberg

[57] ABSTRACT

Phospholipid compositions of the formula:

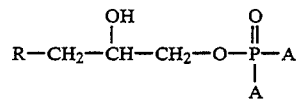

wherein:
A, which may be the same or different or mixtures thereof, are selected from OH, OM, and R—CH₂—CHOH—CH₂—O—;
M is a cation; and
R is a quaternized organosilicone amidoamine moiety of the formula;

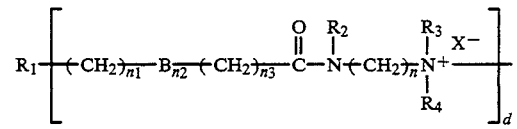

wherein:
$R_1$ is a silicone backbone chain to which amine functional group(s) can be attached.

7 Claims, No Drawings

SILICONE MODIFIED PHOSPHOLIPID COMPOSITIONS

FIELD OF THE INVENTION

The present invention relates to novel organosilicone compounds and, more particularly, to silicone containing derivatives having at least one esterified phosphate group in the molecule.

BACKGROUND OF THE INVENTION

Phosphate esters, quaternary amine compounds, betaines and certain substituted betaines are known in the art and have been commercially used over the years for a variety of applications, including those requiring surfactant properties. More recently, various betaine derivatives having, in general, specific quaternary compounds linked to phosphate esters referred to as phosphobetaines, and more particularly "synthetic phospholipids," have been disclosed, for example, in U.S. Pat. Nos. 4,215,064, 4,233,192 and 4,380,637 to Lindemann et al.; U.S. Pat. Nos. 4,209,449, 4,336,385 and 4,503,002 to Mayhew et al.; and U.S. Pat. Nos. 4,243,602, 4,283,542 and 4,336,386 to O'Lenick et al. These synthetic phospholipids are disclosed as exhibiting outstanding foaming, viscosity building, wetting, cleansing, detergency, anti-static, conditioning and emulsifying properties, making them useful in industrial applications calling for high performance surface active agents. The synthetic phospholipids are also described as being highly stable compositions which are well tolerated by human tissue (i.e. they exhibit exceptionally low oral toxicity and ocular irritation) and, hence, are well suited for use in a variety of personal care applications including cosmetic formulations as well as in industrial processes.

A variety of organosiloxane compositions which exhibit excellent properties as surface active agents are also known and have been used commercially over the years, including for personal care and home care applications. More recently, there have been suggested betaine and phosphobetaine modified organosiloxanes such as disclosed, for example, in U.S. Pat. Nos. 4,609,750 and 4,654,161 to Kollmeier et al. and U.S. Pat. No. 5,091,493 to O'Lenick et al. While certain organosilicone compositions containing phosphobetaines as well as methods for preparing the same are known, there has been no prior disclosure or suggestion of the novel phospholipid compositions of the present invention or of methods for readily preparing silicone modified phospholipid compositions, which permit the preparation of a variety of compositions to achieve a range of properties for different applications.

SUMMARY OF THE INVENTION

It is accordingly an object of the present invention to provide novel silicone-modified phospholipid compositions which exhibit excellent surface-active properties including high foaming, are well tolerated by human tissue, are substantive to the surface of natural and synthetic fiber, and the like.

It is another object of the present invention to provide novel silicone-modified phospholipid compositions containing terminal, lateral (pendant) or combinations of terminal and lateral (pendant) silicone moieties.

In accordance with the present invention, there has now been discovered novel phospholipid compositions that may be represented by the following general formula.

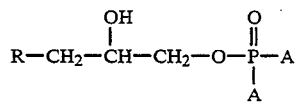

wherein:
A, which may be the same or different or mixtures thereof are selected from OH, OM, and R—CH$_2$—CHOH—CH$_2$—O—;
M is a cation, preferably an alkali metal;
R is a quaternized organosilicone amidoamine moiety of the formula;

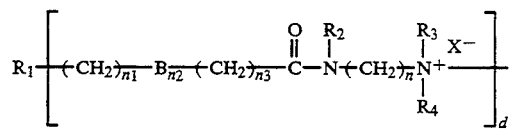

wherein:
R$_1$ is a silicone backbone chain hereinafter described to which amine functional group(s) as herein described can be attached;
R$_2$ is hydrogen or alkyl, hydroxyalkyl or alkenyl of up to 6 carbon atoms each, or cycloalkyl of up to 6 carbon atoms, preferably from 2 to 5 carbon atoms or polyoxyalkylene of up to 10 carbon atoms within the oxyalkylene unit;
R$_3$ and R$_4$, which may be the same or different, are selected from alkyl, hydroxyalkyl, carboxyalkyl of up to 6 carbon atoms;
X$^-$ is at least one and is an anion, preferably a halogen;
n is an integer from 2 to 12;
n$^1$ is zero or an integer from 1 to 12;
n$^2$ is 0 or 1;
n$^3$ is an integer from 1 to 5;
B is sulfur (S) or oxygen (O); with the proviso that when n$^2$ is 0, n$^1$ or n$^3$ is at least 1 and when n$^2$ is 1, n$^1$ and n$^3$ each is at least 1; and
d is one or greater, preferably 2–10.

In addition to the foregoing definitions wherein R is a quaternized organosilicone amidoamine, R may be a quaternized organosilicone amine moiety of the formula:

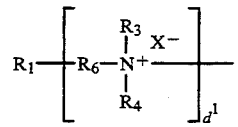

wherein:
R$_1$ is a silicone backbone chain to which amine functional groups as herein described can be attached;
R$_6$ is alkylene, hydroxy alkylene, arylene, alkarylene, aralkylene, heteroalkylene wherein the hetero atom can be N, S, or O and there can be more than one of such hetero atoms in the chain;
X$^-$ is at least one and is an anion, preferably a halogen;
d$^1$ is an integer of one or greater, preferably 2–10;
R$_3$ and R$_4$ are as hereinabove defined.

The silicone backbone chain, $R_1$, to which the amine functional groups as hereinabove described are attached and which are shown herein as $R_{11}$, corresponds to the general formula:

$$R_{11}-\underset{\underset{R_{10}}{|}}{\overset{\overset{R_{10}}{|}}{Si}}-\left[O-\underset{\underset{R_8}{|}}{\overset{\overset{R_7}{|}}{Si}}\right]_e\left[O-\underset{\underset{R_{11}}{|}}{\overset{\overset{R_7}{|}}{Si}}\right]_f O-\underset{\underset{R_{10}}{|}}{\overset{\overset{R_{10}}{|}}{Si}}-R_{11}$$

wherein:

$R_7$ and $R_8$, which may be the same or different are selected from alkyl, aryl, capped or uncapped polyoxyalkylene, alkaryl, aralkylene and alkenyl (vinyl);

$R_{10}$ can be the same or different and can be selected from alkyl, aryl and olefinic (vinyl);

$R_{11}$, which can be the same or different, can be selected from $R_{10}$, $-(CH_2)_{n1}-B_{n2}-(CH_2)_{n3}-CO-NR_2-$ selected from $R_{10}$, $-(CH_2)_{n1}-B_{n2}-(CH_2)_{n3}-CO-NR_2-(CH_2)_n-NR_3R_4$, $-R_6-NR_3R_4-$ and mixtures thereof, wherein $R_2$, $R_3$, $R_4$, $R_6$, B, n, $n^1$, $n^2$ and $n^3$ are as defined above; with the proviso that there must be at least one of $R_{11}$ which is either amidoamine or amine;

e can be an integer of 0 to 50,000;

f can be an integer of 0 to 100.

It is evident from the above general formula for phospholipid compositions of the invention that the functional phosphorus containing group(s) can be linked terminally, laterally or both terminally and laterally to the siloxane backbone chain.

DESCRIPTION OF THE PREFERRED EMBODIMENT

The novel phospholipid compositions of the present invention comprise a class of silicone-modified phospholipid compositions which may be represented by the general formula:

$$R-CH_2-\underset{\underset{}{\overset{\overset{OH}{|}}{CH}}}-CH_2-O-\underset{\underset{A}{|}}{\overset{\overset{O}{\|}}{P}}-A$$

wherein:

A, which may be the same or different or mixtures thereof are selected from OH, OM, and $R-CH_2-CHOH-CH_2-O-$;

M is a cation, preferably an alkali metal;

R is a quaternized organosilicone amidoamine moiety of the formula:

$$R_1-\left[(CH_2)_{\overline{n1}}-B_{\overline{n2}}-(CH_2)_{\overline{n3}}-\overset{\overset{O}{\|}}{C}-\underset{\underset{}{|}}{\overset{\overset{R_2}{|}}{N}}-(CH_2)_{\overline{n}}\underset{\underset{R_4}{|}}{\overset{\overset{R_3}{|}}{N^+}}-\right]_d X^-$$

wherein:

$R_1$ is a silicone backbone chain as hereinafter described to which the amine functional group(s) can be attached;

$R_2$ is hydrogen or alkyl, hydroxyalkyl or alkenyl of up to 6 carbon atoms each, or cycloalkyl of up to 6 carbon atoms, preferably from 2 to 5 carbon atoms, or polyoxyalkylene of up to 10 carbon atoms within the oxyalkylene unit;

$R_3$ and $R_4$, which may be the same or different, are selected from alkyl, hydroxyalkyl, carboxyalkyl of up to 6 carbon atoms;

$X^-$ is at least one and is an anion, preferably a halogen;

n is an integer from 2 to 12;

$n^1$ is zero or an integer from 1 to 12;

$n^2$ is 0 or 1;

$n^3$ is an integer from 1 to 5;

B is sulfur (S) or oxygen (O); with the proviso that when $n^2$ is 0, $n^1$ or $n^3$ is at least 1 and when $n^2$ is 1, $n^1$ and $n^3$ each is at least 1;

d is one or greater, preferably 2-10.

In addition to the foregoing definition wherein R is a quaternized organosilicone amidoamine, R may also be a quaternized organosilicone amine moiety of the formula:

$$R_1-\left[R_6-\underset{\underset{R_4}{|}}{\overset{\overset{R_3}{|}}{N^+}}-\right]_{d^1} X^-$$

wherein:

$R_1$ is a silicone backbone chain as hereinafter described to which amine functional groups can be attached;

$R_6$ is alkylene, hydroxy alkylene, arylene, alkarylene, aralkylene, heteroalkylene wherein the hetero atom can be N, S or O and there can be more than one of such hetero atoms in the chain;

$X^-$ is at least one and is an anion, preferably a halogen;

$d^1$ is an integer of one or greater, preferably from 2 to 10;

$R_3$ and $R_4$ are as hereinabove defined.

The silicone backbone chain $R_1$ to which the amidoamine or amine functional groups as hereinabove shown are attached and which are shown herein as $R_{11}$, corresponds to the general formula:

$$R_{11}-\underset{\underset{R_{10}}{|}}{\overset{\overset{R_{10}}{|}}{Si}}-\left[O-\underset{\underset{R_8}{|}}{\overset{\overset{R_7}{|}}{Si}}\right]_e\left[O-\underset{\underset{R_{11}}{|}}{\overset{\overset{R_7}{|}}{Si}}\right]_f O-\underset{\underset{R_{10}}{|}}{\overset{\overset{R_{10}}{|}}{Si}}-R_{11}$$

wherein:

$R_7$ and $R_8$, which may be the same or different, are selected from alkyl, aryl, capped or uncapped polyoxyalkylene, alkaryl, aralkylene and alkenyl (vinyl);

$R_{10}$ can be the same or different and can be selected from alkyl, aryl and olefinic (vinyl);

$R_{11}$, which can be the same or different, may be selected from $R_{10}$, $-(CH_2)_{n1}-B_{n2}-(CH_2)_{n3}CO-NR_2-(CH_2)_n-NR_3R_4-$, $-R_6-NR_3R_4-$ and mixtures thereof wherein $R_2$, $R_3$, $R_4$, $R_6$, B, n, $n^1$, $n^2$ and $n^3$ are as defined above; with the proviso that there must be at least one of $R_{11}$ which is either amidoamine or amine;

e can be an integer of 0 to 50,000;

f can be an integer of 0 to 100.

It is evident from the general formula of the novel phospholipid compositions of the invention that the functional phosphorus containing group(s) can be linked terminally, laterally or both terminally and laterally to the siloxane chain.

The phospholipid compositions of the invention can be prepared by reacting corresponding silicone-modified amidoamine or amine reactants with phosphate ester halide reactants in appropriate stoichiometric quantities to obtain the desired products of the formula:

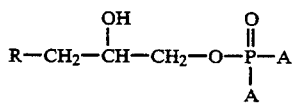

wherein:
  A is as defined hereinabove; and
  R is a quaternized organosilicone amidoamine or amine moiety as defined hereinabove.

The intermediate reactants required in the processes for preparing the phospholipid compositions of the invention can be prepared as follows:

Phosphate ester intermediate reactants utilized can be prepared by known procedures illustrated as follows:

I

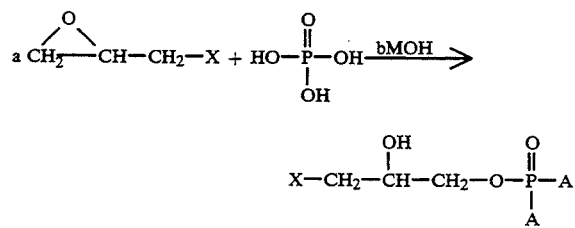

wherein:
  A, which may be the same or different or mixtures thereof, are selected from OH, OM and X—CH$_2$—CHOH—CH$_2$—O—; a is from 1 to 3;
  b is from 1 to 3;
  M is a cation, preferably alkali metal;
  X is halogen; or

II

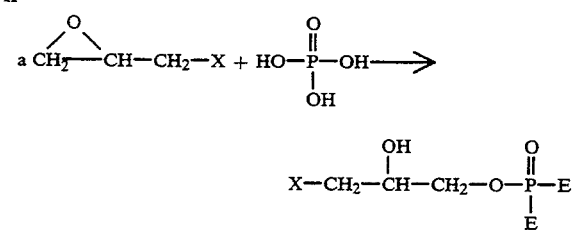

wherein:
  E, which can be the same or different or mixtures thereof are selected from OH and X—CH$_2$—CHOH—CH$_2$O—;
  a is from 1 to 3;
  X is halogen.

Silicone-modified amidoamine intermediate reactants suitable for use in preparing the phospholipid composition of the invention can be prepared as follows:

III

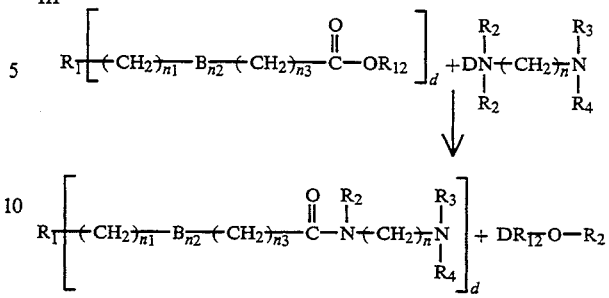

wherein:
  $R_1$ is a silicone backbone chain as herein defined;
  $R_2$ is as previously defined but at least one $R^2$ is hydrogen;
  $R_3$ and $R_4$ is as previously defined;
  $R_{12}$ is hydrogen or alkyl;
  B is sulfur or oxygen; with the proviso that when $n^2$ is 0, $n^1$ or $n^3$ is at least 1 and when $n^2$ is 1, $n^1$ and $n^3$ each is at least 1;
  n is an integer from 2 to 12;
  $n^1$ is zero or an integer of one or greater;
  $n^2$ is 0 or 1;
  $n^3$ is an integer of 1 to 5;
  d and D is an integer from 1 or greater, generally from 1–50 and preferably 2–10. The reactant ratio of the amine reactant to the carboxyl reactant on the silicon is preferably 1:1 but can be varied in ratio of 0.8–1.2.

The above coupling reaction (III) for preparing the silicone-modified amidoamine intermediate reactants can be carried out neat or can be carried out in an inert solvent such as xylene, toluene, benzene, chlorobenzene or the like. While the molecular weight of suitable silicone-modified intermediate amidoamine reactants is not critical, the solubility of such reactants in water or water plus a cosolvent is important and the molecular weight of such reactants is preferably from about 500 to 1500.

The polysiloxane-containing functional carboxylic acids or derivatives thereof (terminal, lateral or combination of terminal and lateral) applicable for use in preparing the silicone-modified amidoamine intermediate reactants as set forth in the reaction sequence illustrated above (III) can be prepared by a variety of known procedures such as illustrated by the following:

IV

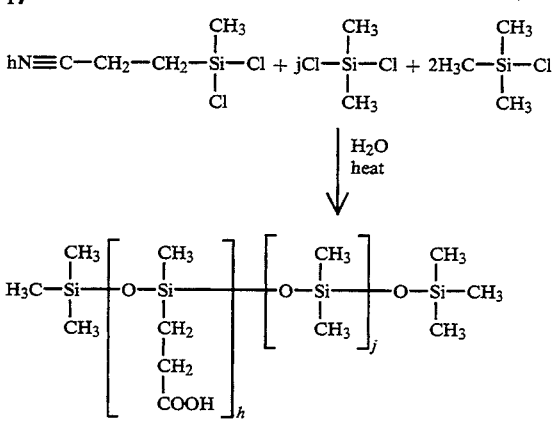

wherein:
 h is an integer from 1–100;
 j is an integer from 0–1000.

V

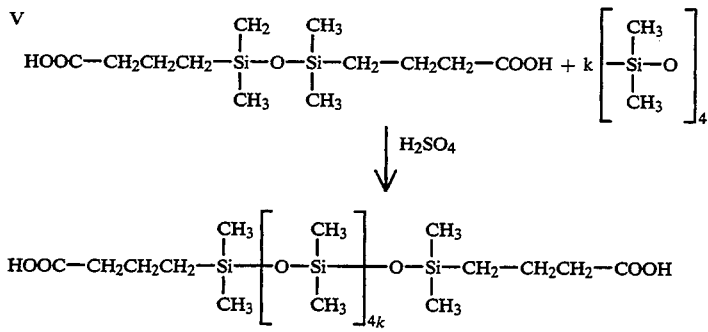

wherein:
 k is an integer from 1–1000.

VI

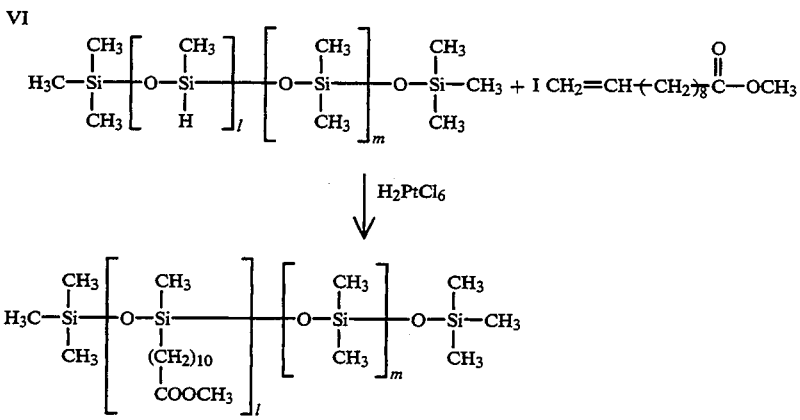

wherein:
 l is an integer from 1–100;
 m is an integer from 0–1000.

Suitable carboxylfunctional silicone compositions having terminal, lateral or combinations of terminal and lateral functional groups are available commercially, for example, from Shin-Etsu. While the molecular weight of the silicone compositions which may be employed are not critical, and suitable compositions may have molecular weights of 5000, or even higher, silicone compositions having molecular weights from about 500 to about 1500 are in general preferred.

Silicone-modified amine intermediate reactants which are suitable for use in preparing alternate embodiments of the silicone-modified phospholipid compositions of the invention can be silicone-modified tertiary amines (terminal, lateral or combinations thereof) which are prepared by a variety of known procedures such as disclosed, for example, in U.S. Pat. No. 3,389,160 which describes the preparation of a carbinol containing tertiary silicone amine encompassing the reaction of a secondary amine with an epoxy containing silicone fluid (example 1) and by Snow et al, J. Langmuir, 1990, 6(2), pp 336–39, wherein the preparation of tertiary amino functional siloxanes result from the hydrosilylation of olefinic tertiary amines with hydride siloxane fluids employing a platinum catalyst.

In addition, the preparation of a suitable functional tertiary amine dimethylsiloxane capped material is disclosed in U.S. Pat. No. 4,918,210, at example 1, part 2 which consists of the Pt catalyzed addition of a terminal hydride containing silicone fluid with N-allyl-diethylamine. In general, silicone containing tertiary amine intermediate reactants which are water soluble or are soluble in water and a cosolvent with molecular weights ranging, between about 500 and 1500 are most advantageously employed.

As noted above, the silicone-modified phospholipid compositions of the invention can be prepared from the silicone-modified amidoamine or silicone-modified tertiary amine reactants with the phosphate ester halide reactants in desired stoichiometric proportions. Such reaction can be carried out in a water solution or in conjunction with a cosolvent such as isopropyl alcohol, ethylene glycol propylene glycol, ethyl cellosolve or the like. The reaction is carried out at a temperature to about 100° C., preferably from about 75° to 95° C., for a time ranging from about 1 to 5 hours and most advantageously for the time necessary for the silicone-modified amine reactant to be substantially completely reacted. The course of the reaction can be determined by amine titration ionic chloride determinations, etc.

The novel silicone-modified phospholipid compositions of the invention are good surfactants and exhibit good foam volume with excellent foam stability. Moreover the phospholipid compositions are non-irritating to the eyes and skin and are highly substantive to fiber surfaces. These compositions are therefore well suited for personal care and home care applications.

The preparation of specific compositions of the invention is illustrated by the following specific examples which are provided herein for purposes of illustration only and are not intended to limit the scope therein.

EXAMPLE 1

Alpha, Omega-Bis (Carboxylalkyl) containing polydimethylsiloxane of the general formula:

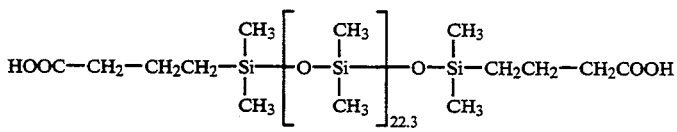

having a molecular weight of about 1956 obtained commercially from Shin-Etsu under the designation X-22162A is used in this example.

195.6 grams (0.1 mole) of the above polysiloxane and 30.6 grams (an excess) of dimethylaminopropyl amine (DMAPA) are charged to a reaction vessel and reacted at a temperature ranging between 150° to 160° C. for four hours followed by vacuum stripping. The product alkali number is found to be 59 (theoretical 55.8) and Acid No. is <1.

75.04 grams of a solution of 40% active phosphate ester halogen reactant prepared by reaction of 3 moles of epichlorohydrin and one mole of sodium dihydrogen phosphate in a solvent system containing 342 grams of a combination of propylene glycol and water in a 2:1 proportion of propylene glycol to water is charged into and combined with 228.2 grams of the reaction mixture above and heated to 75° to 85° C. After a reaction time of 6 hours while heating the reaction mixture at 75° to 85° C., the reaction mixture becomes homogeneous and has a percentage of NaCl of 2.11 (theoretical 2.17). The reaction mixture is cooled and discharged. A clear liquid product is obtained.

The resultant product when added to water formed a clear solution which foamed well, as compared to the silicone fluid starting material which formed hazy non-foaming mixture in water. The foam that is formed is extremely stable.

EXAMPLE 2

A trimethylsilyl capped silicone fluid with a lateral carboxylalkyl group of the general formula:

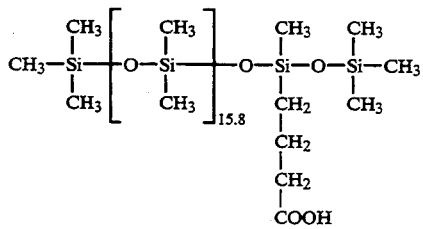

having a molecular weight of about 1578 obtained commercially from Shin-Etsu under the designation X-223710 is used in this example.

157.8 (0.1 moles) grams of the above polysiloxane is admixed with 15.3 grams (an excess) of dimethylaminopropylamine in a reaction vessel and heated to a temperature ranging between 150° to 160° C. The reaction is carried out for four hours at a temperature of 150° to 160° C. while removing water during reaction, followed by vacuum stripping. The alkali number of the reaction mixture is 38.6 and acid number is 0.

A solution of 9.38 grams of 40% active phosphate ester halide reactant prepared by the reaction of 3 moles of epichlorohydrin and 1 mole of sodium dihydrogen phosphate in a solvent mixture of 91 grams of propylene glycol (66%) and water (34%) is charged into and admixed with 43.6 grams of the above reaction mixture and heated to 65° to 75° C. After carrying out the reaction for 6 hours at a temperature of 65° to 75° C., a uniform solution is observed which has a NaCl content of 1%. (theoretical 1.2%).

The reaction mixture is cooled and discharged. A clear liquid product is obtained. When several drops of the product is added to water, a clear solution is formed which produces a great deal of stable foam whereas the original silicone fluid used in the example forms a hazy mixture with water which produces no foam.

EXAMPLE 3

The compound 1,1,1,3,5,5,5 (Heptamethyl) —3—N,-N,—Bis (Hydroxyethyl) Aminopropyl trisiloxane of the general formula:

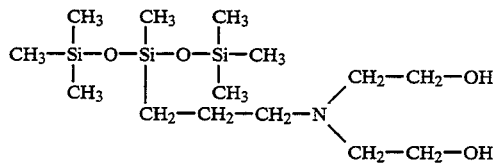

is used in this example. The trisiloxane is prepared by the Filtrol-13 acid clay equilibration of hexamethyl disiloxane with chloropropyl methyl dichlorosilane followed by isolation of the corresponding chloropropyltrisiloxane and the reaction thereof with diethanolamine as described in Snow et al., Langmuir, 1990, Vol. 6, pages 385–391, Example c and e. The trisiloxane composition prepared has a molecular weight of 367.

11.1 grams (0.03 moles) of the above trisiloxane composition is admixed with 9.38 grams (0.01 moles) of a 40% active phosphate ester halide reactant prepared as described in examples 1 and 2 and a solvent mixture containing 14.4 grams isopropyl alcohol and 7.5 grams of water in a reaction vessel. The reaction mixture is heated at a temperature of 85° to 90° C. for 3 hours. A clear liquid product is obtained containing 2.2% NaCl.(theoretical 2.4%). The reaction product forms a clear solution when mixed with water which produces a great deal of stable foam.

EXAMPLE 4

The compound 1,1,1,3,5,5,5 (hepta-methyl), 3-(7-Dimethylamino, 6-Hydroxyl)-4-Oxa Heptatrisiloxane having the formula:

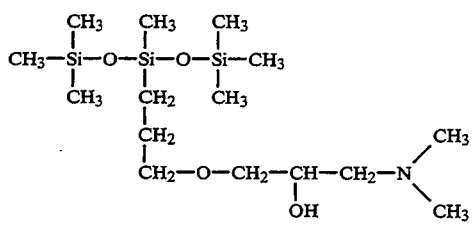

prepared as described in U.S. Pat. No. 3,389,160, Example 1, is used in this example.

37.8 (0.1 moles) of the above siloxane compound is admixed with 31.3 grams (0.033 moles) of a 40% phosphate ester halide reactant prepared as described in examples 1 and 2 and a combination of 44.7 grams isopropanol and 29.9 grams water in a reaction vessel. The reaction mixture is heated to 75° to 85° C. and the reaction is carried out for 4 hours while maintaining the same temperature. A homogenous, colorless liquid is formed having a NaCl content of 3.9%.(theoretical 4.07) which forms a highly foaming clear solution in water.

EXAMPLE 5

Pentamethyl disiloxane is prepared by the sulfuric acid catalyzed reaction between tetramethyldisiloxane and hexamethyl disiloxane. The reaction mixture is washed with ice water and the product is isolated by fractionation.

1-carbomethoxy propyl pentamethyl disiloxane is prepared by the chloroplatinic acid catalyzed addition of pentamethyl disiloxane to methyl vinylacetate.

The 1-carbomethoxy propyl pentamethyl disiloxane is reacted with an excess of dimethyl amino propyl amine in a reaction vessel at a temperature ranging between 150° C. and 160° C. for four hours while collecting the evolved methanol. The reaction product has a molecular weight of 318.

9.54 grams of the amidoamine reaction product (0.03 moles) is admixed in a reaction vessel with 9.38 grams of a solution of 40% active phosphate ester halide reactant prepared by the reaction of 3 moles of epchlorohydrin and 1 mole of sodium diacid phosphate and a cosolvent system consisting of 16.6 grams of isopropyl alcohol and 9 grams of water. The reaction vessel is heated to bring the reaction mixture to a temperature of 75° C. to 80° C., which temperature is maintained for 4 hours at which time a homogeneous solution is obtained. The ionic chlorine content of 3.8 percent is determined as NaCl (theoretical is 3.96).

The reaction products is soluble in water and forms a large volume of stable foam.

Although some preferred embodiments have been described, many modifications and variations may be made thereto in light of the above teachings. It is therefore to be understood that within the scope of the appended claims, the invention may be practiced otherwise than as specifically described and illustrated.

What is claimed is:

1. Phospholipid compositions of the formula:

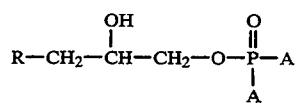

wherein:

A, which may be the same or different or mixtures thereof, are selected from OH, OM, and R—CH$_2$—CHOH—CH$_2$—O—;

M is a cation; and

R is a quaternized organosilicone amidoamine moiety of the formula:

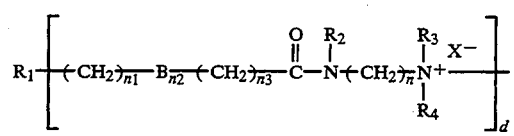

wherein:

$R_1$ is a silicone backbone chain to which amine functional group(s) can be attached;

$R_2$ is hydrogen or alkyl, hydroxyalkyl or alkenyl of up to 6 carbon atoms each, or cycloalkyl of up to 6 carbon atoms, preferably from 2 to 5 carbon atoms or polyoxyalkylene of up to 10 carbon atoms within the oxyalkylene unit;

$R_3$ and $R_4$, which may be the same or different, are selected from alkyl, hydroxyalkyl, carboxyalkyl of up to 6 carbon atoms;

$X^-$ is an anion;

n is an integer from 2 to 12;

$n^1$ is zero or an integer from 1 to 12;

$n^2$ is 0 or 1;

$n^3$ is an integer from 1 to 5;

B is sulfur (S) or oxygen (O); with the proviso that when $n^2$ is 0, $n^1$ or $n^3$ is at least 1 and when $n^2$ is 1, $n^1$ and $n^3$ each is at least 1; and d is one or greater; or R is a quaternized organosilicone amine moiety of the formula:

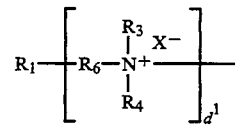

wherein:

$R_1$ is a silicone backbone chain to which amine functional groups can be attached;

$R_6$ is alkylene, hydroxy alkylene, arylene, alkarylene, aralkylene, heteroalkylene wherein the hetero atom can be N, S, or O and there can be more than one of such hetero atoms in the chain;

$X^-$ is an anion;

$d^1$ is one or greater; and $R_3$ and $R_4$, which may be the same or different, are selected from alkyl, hydroxyalkyl, carboxyalkyl of up to 6 carbon atoms.

2. The phospholipid compositions as claimed in claim 1, wherein silicone backbone chain $R_1$ to which amine functional groups $R_{11}$ can be attached is of the formula:

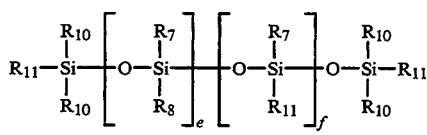

wherein:
- $R_7$ and $R_8$, which may be the same or different, are selected from alkyl, aryl, capped or uncapped polyoxyalkylene, alkaryl, aralkylene and alkenyl (vinyl);
- $R_{10}$ can be the same or different and can be selected from alkyl, aryl and olefinic (vinyl);
- $R_{11}$, which can be the same or different, can be selected from $R_{10}$, $-(CH_2)_{n1}-B_{n2}-(CH_2)_{n3}-CO-NR_2-(CH_2)_n-NR_3R_4$, $-R_6-NR_3R_4-$ and mixtures thereof, wherein $R_2$, $R_3$, $R_4$, $R_6$, B, n, $n^1$, $n^2$ and $n^3$ are as defined above; with the proviso that there must be at least one of $R_{11}$ which is either amidoamine or amine;
- e can be an integer of 0 to 50,000;
- f can be an integer of 0 to 100.

3. The phospholipid compositions as claimed in claim 1, wherein R is a quaternized organosilicone amidoamine moiety of the formula:

$$R_1 \left[ -(CH_2)_{\overline{n1}}-B_{\overline{n2}}-(CH_2)_{\overline{n3}}-\overset{O}{\underset{\|}{C}}-\overset{R_2}{\underset{|}{N}}-(CH_2)_{\overline{n}}\overset{R_3}{\underset{|}{\overset{|}{N^+}}}\overset{X^-}{\underset{R_4}{|}} \right]_d$$

wherein:
- $R_1$ is a silicone backbone chain to which amine functional group(s) can be attached;
- $R_2$ is hydrogen or alkyl, hydroxyalkyl or alkenyl of up to 6 carbon atoms each, or cycloalkyl of up to 6 carbon atoms, preferably from 2 to 5 carbon atoms or polyoxyalkylene of up to 10 carbon atoms within the oxyalkylene unit;
- $R_3$ and $R_4$, which may be the same or different, are selected from alkyl, hydroxyalkyl, carboxyalkyl of up to 6 carbon atoms;
- $X^-$ is an anion;
- n is an integer from 2 to 12;
- $n^1$ is zero or an integer from 1 to 12;
- $n^2$ is 0 or 1;
- $n^3$ is an integer from 1 to 5;
- B is sulfur (S) or oxygen (O); with the proviso that when $n^2$ is 0, $n^1$ or $n^3$ is at least 1 and when $n^2$ is 1, $n^1$ and $n^3$ each is at least 1; and
- d is one or greater.

4. The phospholipid compositions as claimed in claim 3 wherein the silicone backbone chain $R_1$ to which amine functional groups $R_{11}$ can be attached is of the formula:

$$R_{11}-\underset{R_{10}}{\overset{R_{10}}{\underset{|}{\overset{|}{Si}}}}-O-\left[\underset{R_8}{\overset{R_7}{\underset{|}{\overset{|}{Si}}}}-O\right]_e \left[\underset{R_{11}}{\overset{R_7}{\underset{|}{\overset{|}{Si}}}}-O\right]_f \underset{R_{10}}{\overset{R_{10}}{\underset{|}{\overset{|}{Si}}}}-R_{11}$$

wherein:
- $R_7$ and $R_8$, which may be the same or different, are selected from alkyl, aryl, capped or uncapped polyoxyalkylene, alkaryl, aralkylene and alkenyl (vinyl);
- $R_{10}$ can be the same or different and can be selected from alkyl, aryl and olefinic (vinyl);
- $R_{11}$, which can be the same or different, can be selected from $R_{10}$, $-(CH_2)_{n1}-B_{n2}-(CH_2)_{n3}-CO-NR_2-(CH_2)_n-NR_3R_4$, $-R_6-NR_3R_4-$ and mixtures thereof, wherein $R_2$, $R_3$, $R_4$, $R_6$, B, n, $n^1$, $n^2$ and $n^3$ are as defined above; with the proviso that there must be at least one of $R_{11}$ which is an amidoamine;
- e can be an integer of 0 to 50,000; and
- f can be an integer of 0 to 100.

5. The phospholipid compositions as claimed in claim 1, wherein M is an alkali metal, d is from 2 to 10 and $d^1$ is from 2 to 10.

6. The phospholipid compositions as claimed in claim 1, wherein $X^-$ is a halogen.

7. The phospholipid compositions as claimed in claim 4, wherein M is an alkali metal, d is from 2 to 10 and $X^-$ is a halogen.

* * * * *